US008033174B2

(12) United States Patent
Shin et al.

(10) Patent No.: US 8,033,174 B2

(45) Date of Patent: Oct. 11, 2011

(54) ULTRASOUND DIAGNOSTIC SYSTEM

(75) Inventors: Soo Hwan Shin, Seoul (KR); Kyo Jong Koo, Seoul (KR); Young Seuk Song, Seoul (KR)

(73) Assignee: Medison Co. Ltd., Kangwon-Do (KR)

( * ) Notice: Subject to any disclaimer, the term of this patent is extended or adjusted under 35 U.S.C. 154(b) by 384 days.

(21) Appl. No.: 12/206,641

(22) Filed: Sep. 8, 2008

(65) Prior Publication Data

US 2009/0069690 A1 Mar. 12, 2009

(30) Foreign Application Priority Data

Sep. 7, 2007 (KR) ........................ 10-2007-0091154
Oct. 12, 2007 (KR) ........................ 10-2007-0103117

(51) Int. Cl.
*G01N 9/18* (2006.01)
*A61B 8/14* (2006.01)

(52) U.S. Cl. .............. 73/661; 73/606; 73/607; 600/437; 600/459

(58) Field of Classification Search .................... 73/661, 73/606, 607; 600/437, 459
See application file for complete search history.

(56) References Cited

U.S. PATENT DOCUMENTS 5,318,027 A * 6/1994 Fukui ............................ 600/437
5,505,203 A * 4/1996 Deitrich et al. ............... 600/437
5,657,761 A * 8/1997 Okada et al. .................. 600/437
5,882,310 A * 3/1999 Marian, Jr. .................... 600/459
6,500,126 B1 * 12/2002 Brock-Fisher ................ 600/459
6,629,928 B1 * 10/2003 Dolan et al. .................. 600/437
2001/0023318 A1 9/2001 Miyaki
2003/0229281 A1 12/2003 Barnard et al.

FOREIGN PATENT DOCUMENTS

JP 05-168625 7/1993
JP 11-299781 11/1999
JP 2005-168885 6/2005
JP 2005-528950 9/2005
KR 2007-0002131 1/2007

OTHER PUBLICATIONS

Korean Office Action issued in Korean Patent Application No. KR 10-2007-0103117 dated Mar. 21, 2011.

* cited by examiner

*Primary Examiner* — J M Saint Surin

(74) *Attorney, Agent, or Firm* — McDermott Will & Emery LLP

(57) ABSTRACT

The present invention relates to an ultrasound diagnostic system. The ultrasound diagnostic system includes a plurality of connectors. Each of the connectors has a signal transmitter to transmit an identification signal uniquely identifying the respective connector. The ultrasound diagnostic system further includes a plurality of probes. Each of the probes has a signal detector and an indicator assembly. In response to a connection of each of the probes to one of the connectors, the signal detector of the respective probe is configured to detect the identification signal identifying said one of the connectors and the indicator assembly of the respective probe is configured to provide an identification of said one of the connectors based on the identification signal.

7 Claims, 4 Drawing Sheets

2
1
10a
10b
10c
10d
3
12d
12c
12b
12a
11a
11b
11c
11d

ULTRASOUND DIAGNOSTIC SYSTEM

The present application claims priority from Korean Patent Application Nos. 10-2007-0091154 and 10-2007-0103117 respectively filed on Sep. 7, 2007 and Oct. 12, 2007, the entire subject matters of which are incorporated herein by reference.

BACKGROUND OF THE INVENTION

1. Technical Field

The present invention generally relates to ultrasound diagnostic systems, and more particularly to an ultrasound diagnostic system capable of identifying a connection status of a probe.

2. Background Art

An ultrasound diagnostic system has become an important and popular diagnostic tool due to its non-invasive and non-destructive nature. Modern high-performance ultrasound imaging diagnostic systems and techniques are commonly used to produce two- or three-dimensional images of internal features of patients.

An ultrasound diagnostic system generally adopts a probe containing an array of piezoelectric elements to transmit and receive ultrasound signals. The ultrasound diagnostic system forms an image of human internal tissues by electrically exciting transducer elements to generate ultrasound signals that travel into the body. Echoes reflected from tissues and organs return to the transducer element and are converted into electrical signals, which are amplified and processed to produce ultrasound data. The ultrasound diagnostic system may adopt various types of probes according to diagnosis purposes.

Since multiple probes are used in the ultrasound diagnostic system, it may be confusing to identify whether or not a desirable probe is appropriately connected. Particularly, since the ultrasound diagnostic system is used in a dark environment, it is difficult to identify which probe is connected.

DETAILED DESCRIPTION OF THE INVENTION

Figure 1:
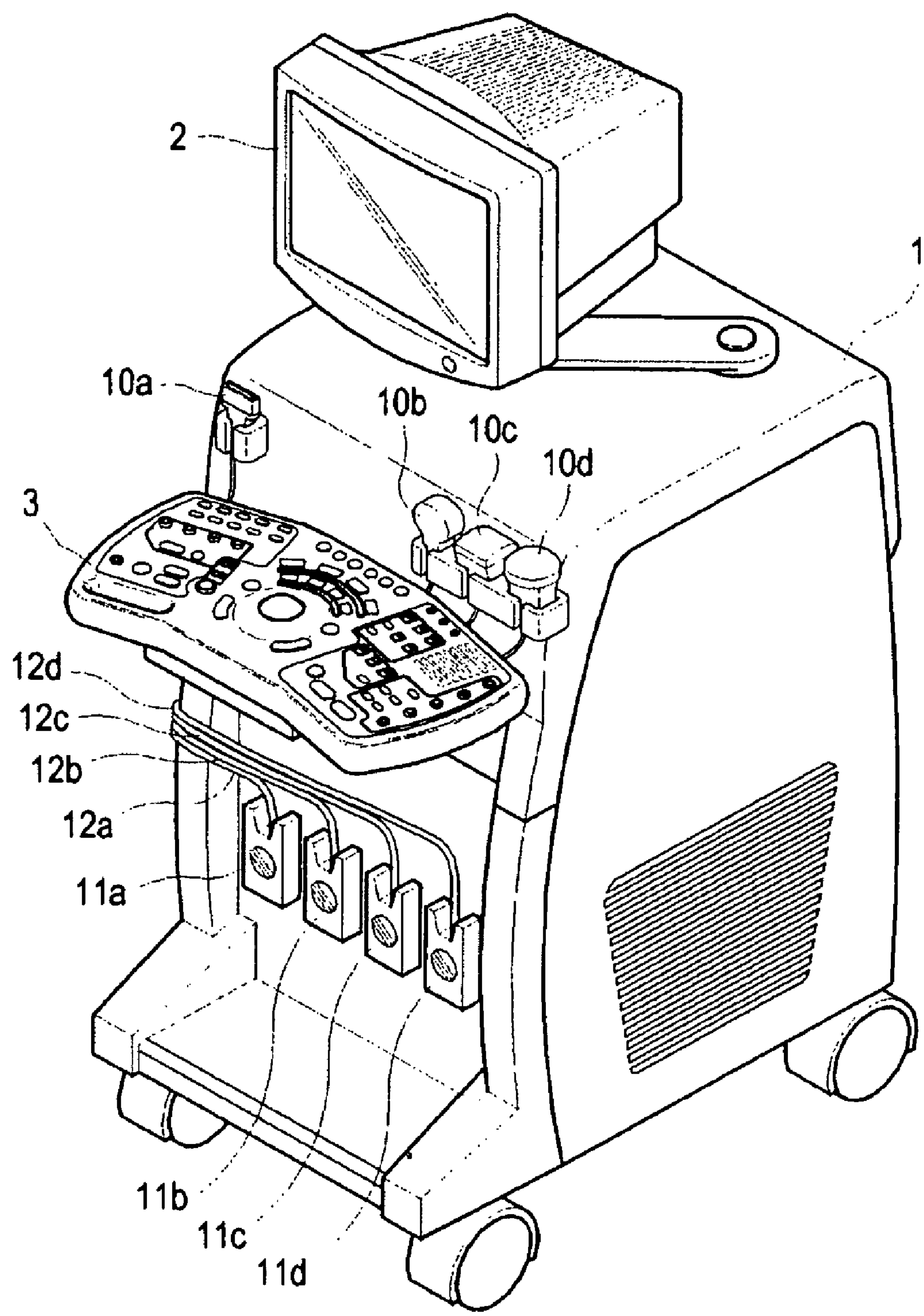
FIG. 1 is a perspective view of an illustrative embodiment of an ultrasound diagnostic system.

FIG. 1 is a schematic diagram showing an illustrative embodiment of an ultrasound diagnostic system. As shown in FIG. 1, the ultrasound diagnostic system 100 may include a body 1, a display unit 2 and a control panel 3. The body 1 may include a plurality of processors such as digital processing units, scan converters and the like. The display unit 2 may be an LCD monitor, a CRT monitor or the like. The control panel 3 may provide a user input interface for allowing the user to input operation instructions. A plurality of connectors 11*a*, 11*b*, 11*c* and 11*d* are provided in the ultrasound diagnostic system 100. Preferably, the connectors 11*a*, 11*b*, 11*c* and 11*d* may be mounted on a front side of the body 1. A plurality of connector cables 12*a*, 12*b*, 12*c* and 12*d* may be provided to connect the connectors 11*a*, 11*b*, 11*c* and 11*d* with the body 1. In the one embodiment, the body may further include an identification signal generator for generating connector identification signals.

Figure 2:
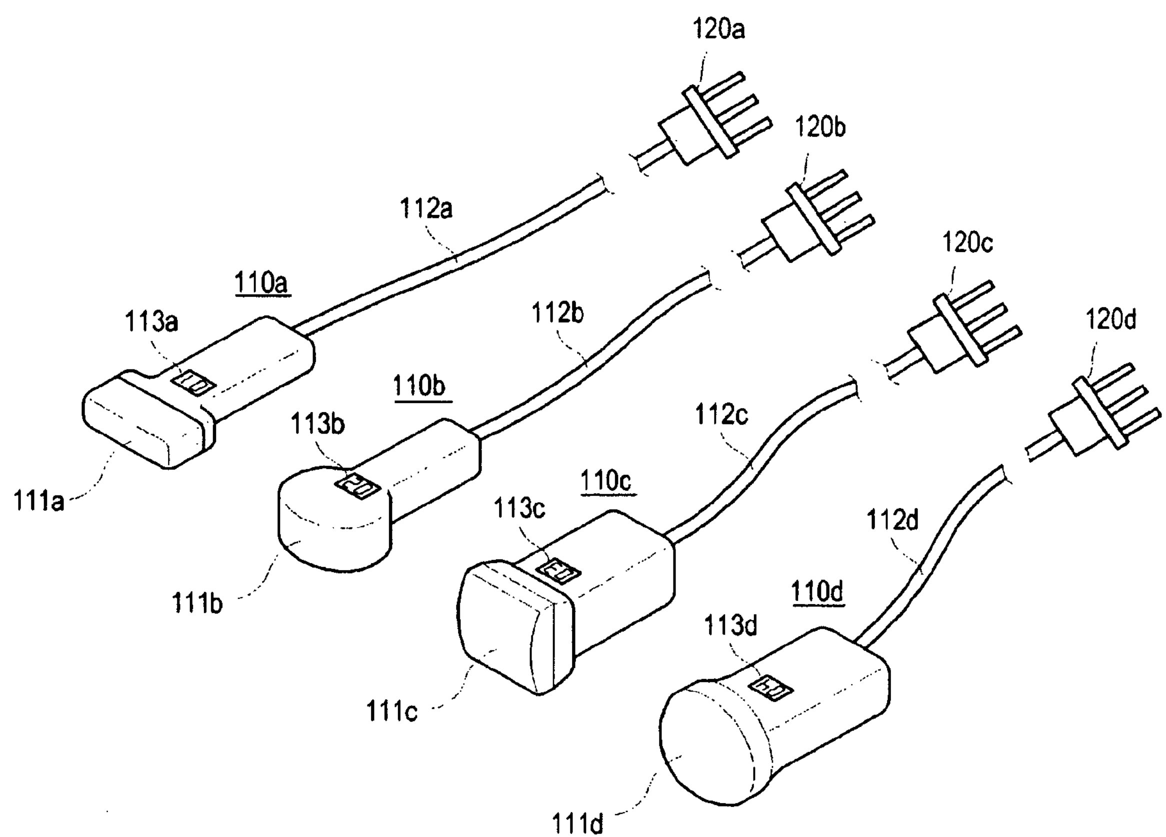
FIG. 2 is a perspective view of illustrative embodiments of various types of probes.

A plurality of probes 10*a*, 10*b*, 10*c* and 10*d* are equipped at predetermined portions of the body 1 in the ultrasound diagnostic system. Various types of the probes may be adopted such as a convex probe, a linear probe, a phased probe, an endocavity probe and the like. The probes may have different uses depending on the diagnosis purpose or method. That is, the probes 10*a*, 10*b*, 10*c* and 10*d* may be alternately used while the ultrasound diagnostic system operates. As illustrated in FIG. 2, the probes 110*a*, 110*b*, 110*c* and 110*d* may be configured with bodies 111*a*, 111*b*, 111*c* and 111*d*, probe cables 112*a*, 112*b*, 112*c* and 112*d*, and plugs 120*a*, 120*b*, 120*c* and 120*d*. The bodies 111*a*, 111*b*, 111*c* and 111*d* may be provided at one end of the probe cables 112*a*, 112*b*, 112*c* and 112*d*. The plugs 120*a*, 120*b*, 120*c* and 120*d* may be male plugs and provided at the other end of the respective probe cables 112*a*, 112*b*, 112*c* and 112*d*. The probes 110*a*, 110*b*, 110*c* and 110*d* may be connected to connectors 11*a*, 11*b*, 11*c* and 11*d* with the plugs 120*a*, 120*b*, 120*c* and 120*d*.

In one embodiment, indicators 113*a*, 113*b*, 113*c* and 113*d* are mounted on a predetermined portion of the probe bodies 111*a*, 111*b*, 111*c* and 111*d*. Each of the indicators may be embodied with a liquid crystalline device, a thin film transistor liquid crystalline device, an organic electro luminescence display, a 7-segment light emitting device display or the like. Each of the indicators may be mounted on a predetermined portion of the corresponding probe body. Each of the probes 111*a*, 111*b*, 111*c* and 111*d* may include a driver for driving the indicators 113*a*, 113*b*, 113*c* and 113*d* so as to be operable to indicate an identification symbol for identifying connection between the probe and the connector. The identification symbols may include a predetermined serial number indicating the connector connected to the corresponding probe.

Figure 3:
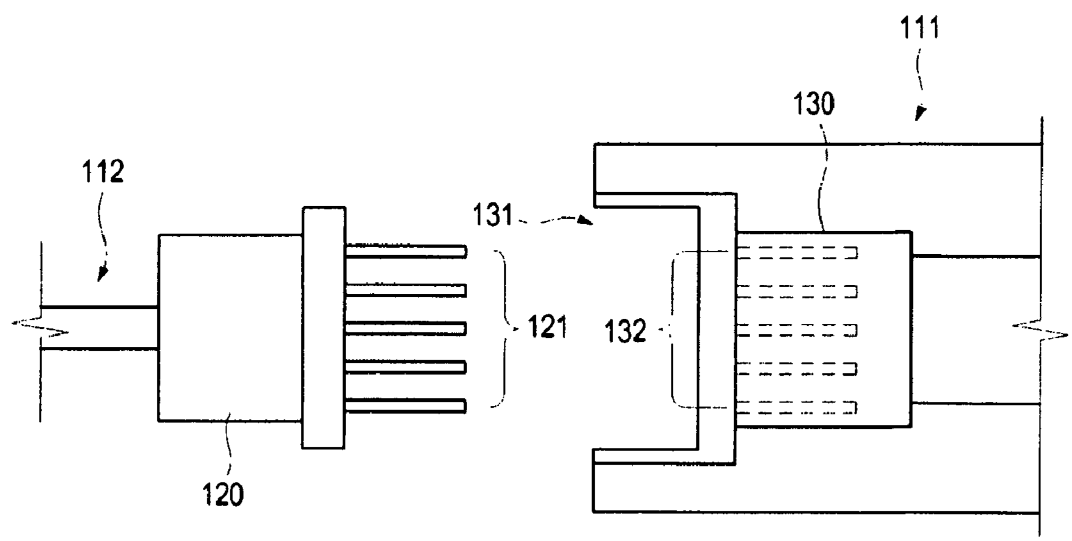
FIG. 3 is a cross-sectional view of an illustrative embodiment of a plug of a probe and a connector in an ultrasound diagnostic system.

FIG. 3 is a cross-sectional view of a plug of the probe and a connector mounted on a body of an ultrasound diagnostic system. As illustrated in FIG. 3, the plug 120 may include a plurality of pins 121. The connector 111 may include a groove 131 which is to be fitted with the plug housing and a socket 130. The socket 130, which is a female socket, may have a plurality of openings 132 corresponding to the respective pins 121 of the plug 121 at an inside one plane of the groove 131. Preferably, the socket 130 may be provided at a plane facing the plug 120.

When the plug 120 is connected to the socket 130 of the connector 111, the connector identification signals generated from the identifier signal generator 140 are transmitted to the probe 110 through the probe cable 112. The driver in the probe 110 may drive the indicator to indicate the identification symbol based on the connector identification signals. The probe 110 may further include a decoder to decode the identification signals.

Figure 4:
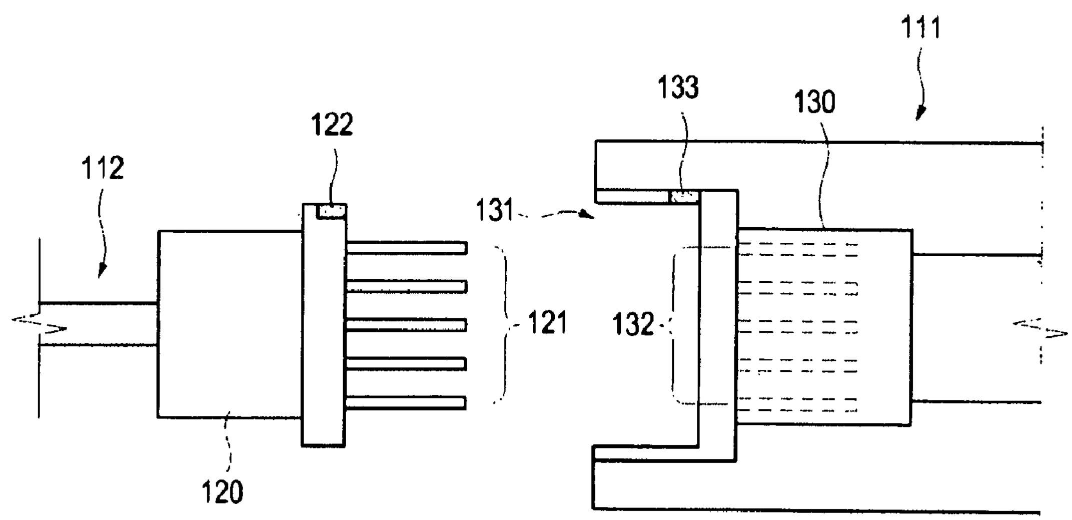
FIG. 4 is a cross-sectional view of an illustrative embodiment of a plug of a probe and a connector with a signal detector and a signal transmitter mounted in one embodiment.

FIG. 4 is a schematic diagram showing an exemplary embodiment of the plug and the socket with a signal detector and a signal transmitter mounted. As illustrated in FIG. 4, a signal transmitter 133 may be mounted at an inside of the groove 131 of the connector 111. The signal transmitter 133 may be built at an edge side of connector housing such that the reception of the plug 120 is not obstructed. The connector identification signals generated from the identification signal generator may be transmitted by the signal transmitter 133. The signal detector 122 may be mounted on the plug housing to be faced with the signal transmitter 133 when the pins 121 of the plug 120 are inserted into the socket 131. That is, when the plug 120 is connected to the socket 130, the signal detector 122 of the plug 120 may detect the identification signals transmitted from the signal transmitter 133. The detected identification signals are transmitted to the driver of the probe 110. Various types of the devices may be adopted as the signal transmitter and the signal detector. In one embodiment, for example, the signal transmitter may be a radio frequency (RF) tag and the signal detector may be a RF reader. Also, the signal transmitter may be a magnetic substance forming a specific magnetic field and the signal detector may be a hall sensor detecting the magnetic field of the magnetic substance.

Figure 5:
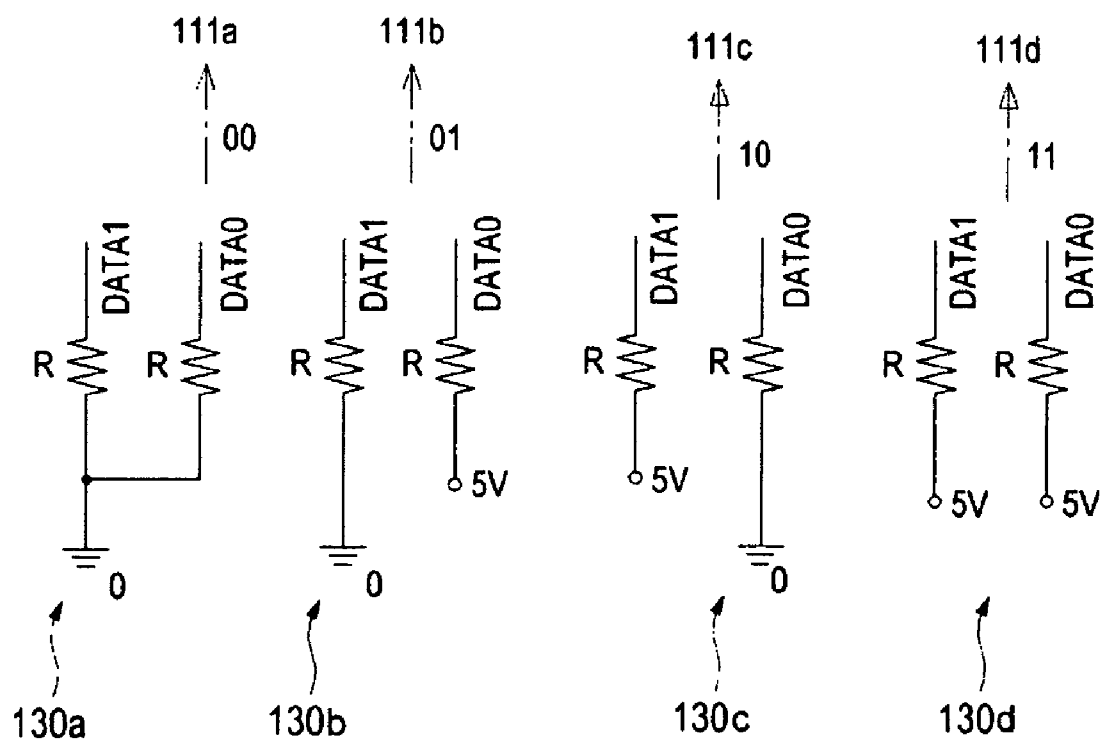
FIG. 5 is a circuit diagram of an illustrative embodiment of an example of an identification signal generator in one embodiment.

FIG. 5 is a circuit diagram of exemplary identification signal generators in one embodiment. A plurality of binary signal generators may be adopted as the identification signal generators in one embodiment. An example of generating four identification signals is illustrated in FIG. 5. Each of the identification generators 130*a*, 130*b*, 130*c* and 130*d* may include two data lines DATA0 and DATA1. Each of the identification generators may generate binary connector identification signals such as '00', '01', '10' and '11' according to connection of the data lines to ground or 5V power. The binary signals of '00', '01', '10' and '11', which are generated from the identification generators 130*a*, 130*b*, 130*c* and 130*d*, may be transmitted to the signal processing unit of the probe. However, the identification signal generator mentioned above may not be limited thereto. Any device capable of providing identification signals of the connectors to the decoder of the probe may be adopted. Although two data lines are used in one embodiment, the number of the data lines is certainly not limited thereto. The number of the data lines may be modified according to the number of the connectors.

The decoder in the probe may be operable to decode the identification signals uniquely identifying one of the connectors. Further, the driver may be operable to drive the indicator to the identification symbol indicating the connected connector. This is so that the user can visually identify the connector connected to the corresponding probe. For example, the indicator may indicate the connected connector with a decimal number.

The respective probe cables 112*a*, 112*b*, 112*c* and 112*d* may be coated with different colors of fluorescent materials or phosphorescence materials so as to be easily identified at a dark place in another embodiment.

As mentioned above, since the indicators indicating whether the probe is connected to the body of the ultrasound image device are provided at the respective probes in accordance with one embodiment, the user may easily identify the connection of the probe with the connector of the body. Also, since the probe cables are coated with different colors of the fluorescent materials or the phosphorescence materials, the user may easily arrange the probe cables at the dark place. Further, the probe cables may be coated with different coating patterns. For example, a check pattern, a stripe pattern, a dot pattern and the like may be adopted to the respective probe cables.

In accordance with one embodiment of the present invention, there is provided a ultrasound diagnostic system comprising: a plurality of connectors, each having a signal transmitter to transmit an identification signal uniquely identifying the respective connector; and a plurality of probes each having a signal detector and an indicator assembly, wherein in response to a connection of each of the probes to one of the connectors, the signal detector of the respective probe is configured to detect the identification signal identifying said one of the connectors, and wherein the indicator assembly of the respective probe is configured to provide an identification of said one of the connectors based on the identification signal.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound diagnostic system, comprising:

a plurality of connectors each having a signal transmitter to transmit an identification signal uniquely identifying the respective connector; and a plurality of probes each having a signal detector and an indicator assembly, wherein in response to a connection of each of the probes to one of the connectors, the signal detector of the respective probe is configured to detect the identification signal identifying said one of the connectors, wherein the indicator assembly of the respective probe is configured to provide an identification of said one of the connectors based on the identification signal, wherein each of the connectors is configured with a groove and the signal transmitter is installed within the groove, wherein each of the probes includes a body, a probe cable and a plug installed at one end of the cable, and wherein the signal detector is mounted on the plug and the indicator assembly including an indicator and a driver for driving the indicator is installed in the body.

2. The ultrasound diagnostic system of claim 1, wherein the identification signal generator includes a plurality of data lines, wherein each of the data lines is configured to generate a binary signal, and wherein the indicator assembly further includes a decoder for decoding the identification signals.

3. The ultrasound diagnostic system of claim 2, wherein the signal transmitter is a radio frequency (RF) tag and the signal detector is a RF reader.

4. The ultrasound diagnostic system of claim 2, wherein the signal transmitter is a magnetic substance forming a specific magnetic field, and wherein the signal detector is a hole sensor for detecting the magnetic field of the magnetic substance.

5. The ultrasound diagnostic system of claim 2, wherein the indicator is selected from a group consisting of a liquid crystalline device, a thin film transistor liquid crystalline device, an organic electro luminescence display and a 7-segment light emitting device display.

6. The ultrasound diagnostic system of claim 1, wherein the cable is coated with different colors of fluorescent materials or phosphorescence materials.

7. The ultrasound diagnostic system of claim 1, wherein the cable is coated with different coating patterns.

* * * * *